United States Patent [19]

Friswell et al.

[11] 4,117,727

[45] Oct. 3, 1978

[54] BUBBLE SENSOR AND METHOD

[76] Inventors: David R. Friswell, 394 Gorwin Dr., Holliston, Mass. 01746; Burleigh M. Hutchins, 59 Lakewood Dr., North Attleboro, Mass. 02760

[21] Appl. No.: 859,531

[22] Filed: Dec. 12, 1977

[51] Int. Cl.$^2$ .............................................. G01N 1/10
[52] U.S. Cl. .................................... 73/422 GC; 73/19
[58] Field of Search ......... 73/19, 37, 423 A, 422 GC, 73/61.1 C

[56] References Cited

U.S. PATENT DOCUMENTS

| | | | |
|---|---|---|---|
| 2,138,141 | 11/1938 | Cromer et al. | 73/19 |
| 3,344,656 | 10/1967 | Van Horne et al. | 73/37 |

Primary Examiner—S. Clement Swisher

[57] ABSTRACT

The bubble sensor is embodied in a liquid chromatographic system. In the exemplified system a sample conduit or loop which is already filled with liquid eluent communicates with the bore of a needle. The opening of the needle bore is immersed in a liquid sample so that the sample may be backfilled into the sample loop by the withdrawal of the syringe which communicates with the sample loop. After the liquid sample has been drawn into the sample conduit, the needle is lifted from the sample source and moved toward a final position in which the sample conduit will be placed in parallel with a primary conduit, so that the pump which pumps the liquid eluent will drive the sample from the opening toward the chromatrographic column. As the needle is being raised toward this position, it is stopped at an intermediate position in which the orifice is sealed. In this condition, the liquid sample is within the sample conduit which is part of a closed space between the orifice and the syringe. The syringe is now driven a small distance to reduce the volume of that space by a predetermined, programmed increment. The pressure before and after the change in the space may be compared to indicate the presence or absence of a bubble in the sample. A preferred way of proceeding is to determine the number of incremental changes of predetermined volume to bring the change in pressure up to a predetermined point, for example, 30 psig. If the number of such incremental changes is less than a predetermined number, then it may be presumed that the sample is free of bubble. If the number is greater than the predetermined number, a possible bubble inclusion is indicated and further action may be taken as more fully described hereinafter.

25 Claims, 12 Drawing Figures

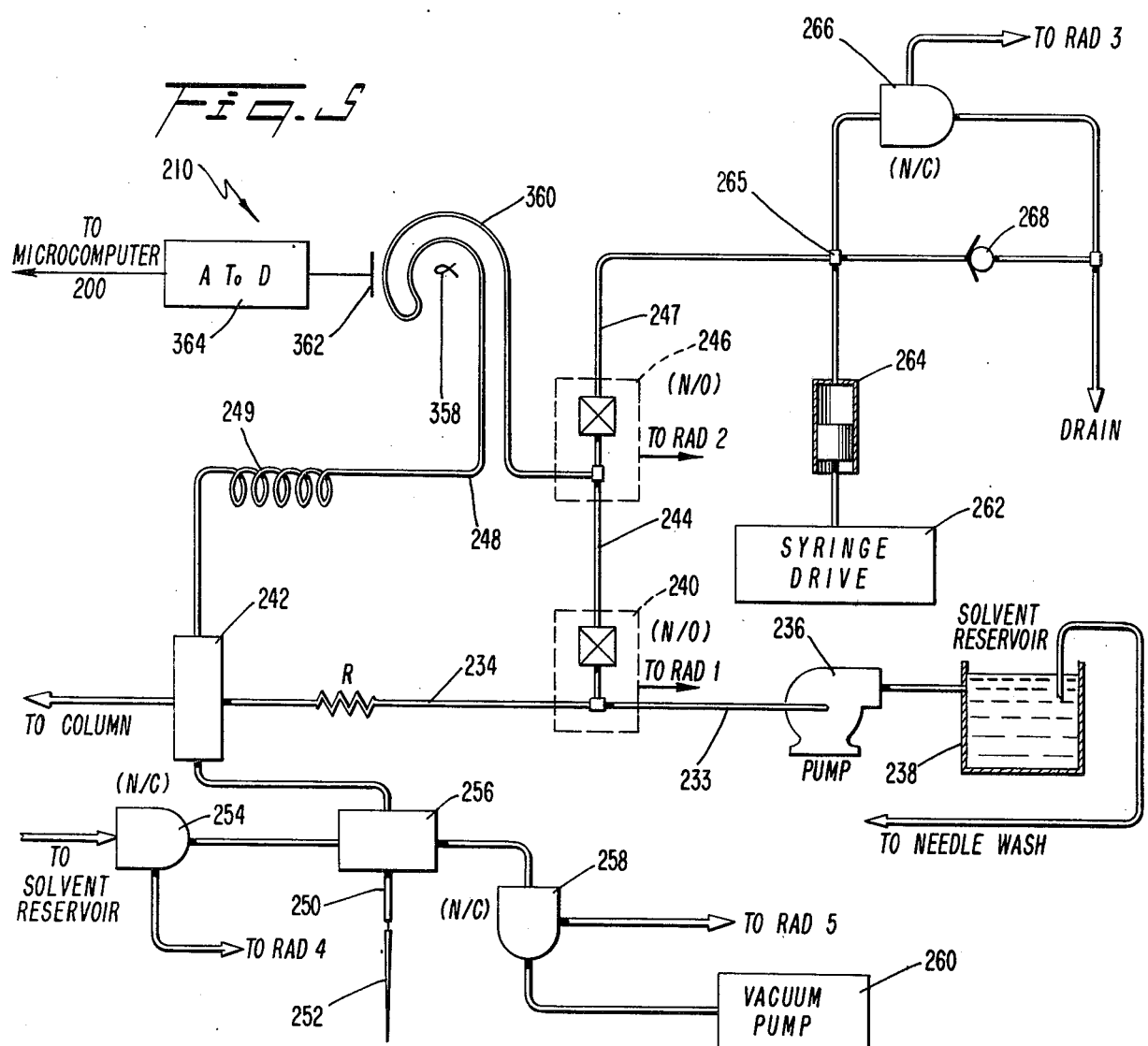
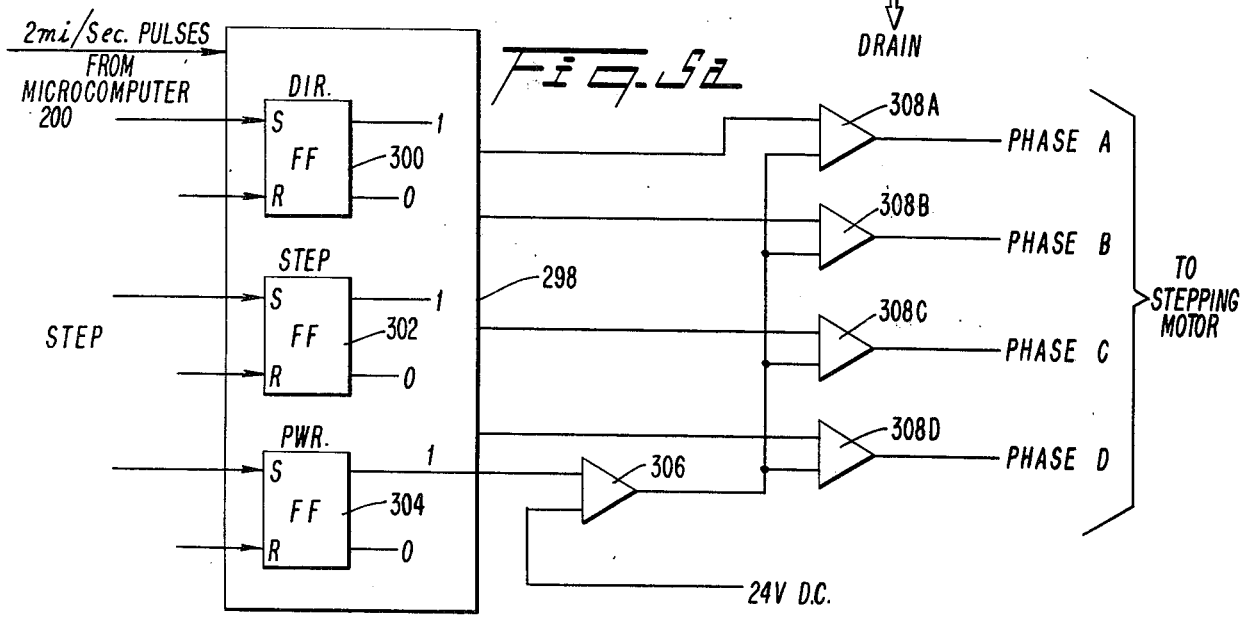

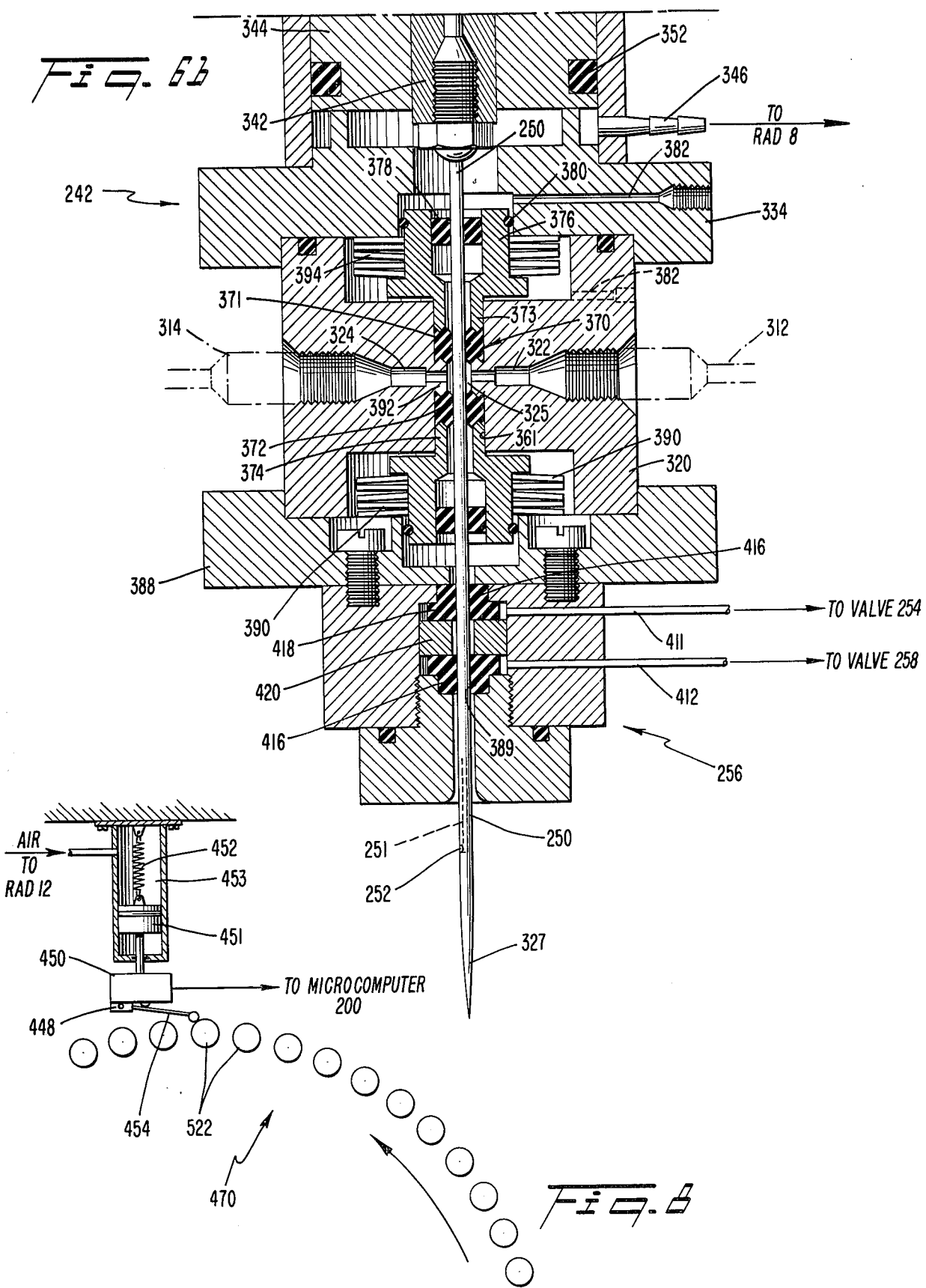

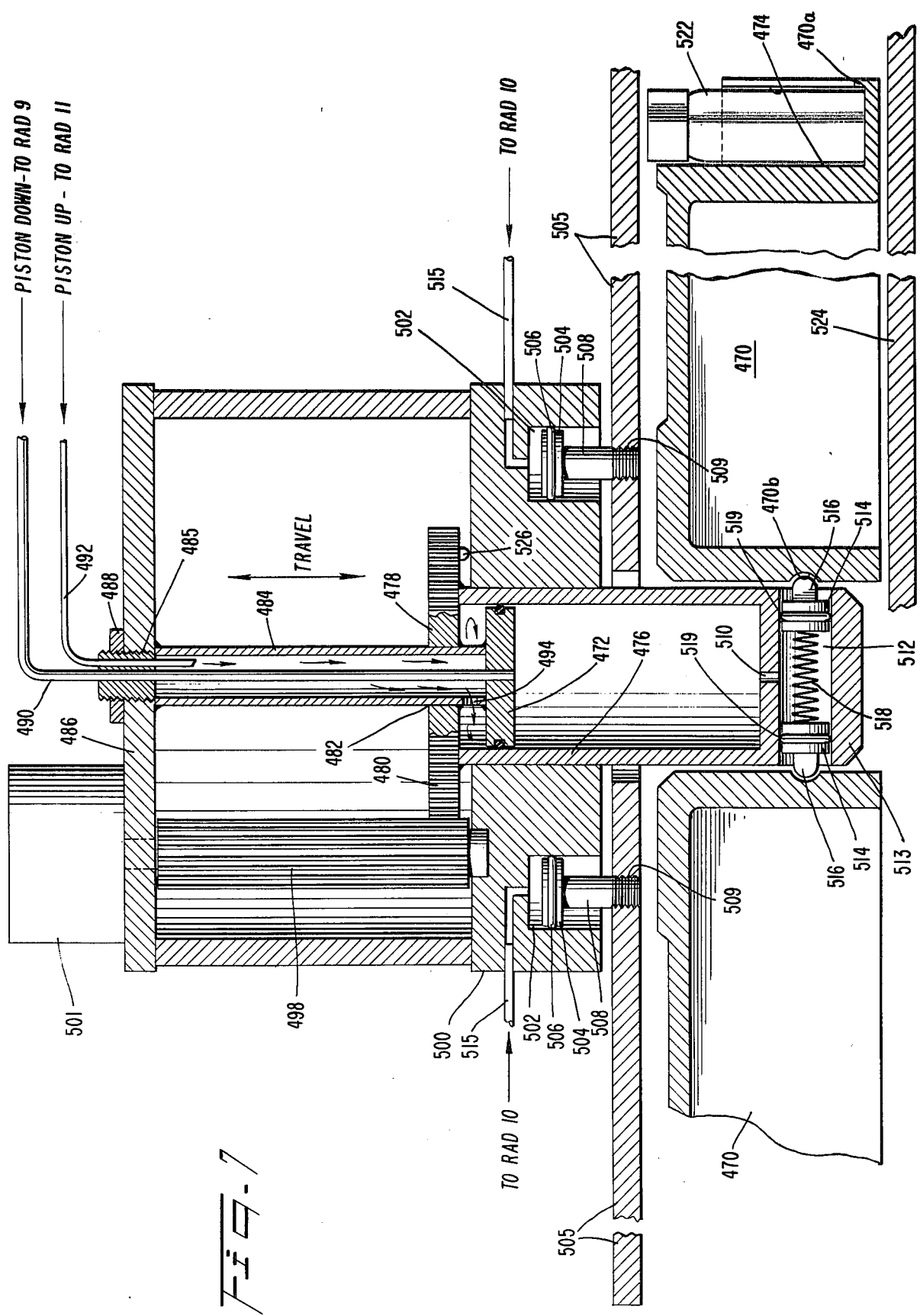

BUBBLE SENSOR AND METHOD

BACKGROUND OF THE INVENTION

One of the problems in liquid chromatography is the injection of a sample into the chromatographic column free of the inclusion of bubbles or gas. Such inclusion may result from so-called cavitation, in which, for example, because of turbulence and perhaps a momentary small drop in pressure some portion of the liquid sample is vaporized to create a bubble. Such inclusion may also occur by the failure to completely immerse into the liquid the aperture or orifice through which the sample is intended to pass into a sample conduit prior to injection. Bubble inclusion in the injection may result in the chromatograph providing poor or even false results. Peak spreading may result. Large inclusion of air or gas may upset or alter the balance of the column and the detector so that a lengthy equilibration time must be attended while the column is flushed with eluent. Visual observation is often inadequate for the timely detection of bubble inclusion whether small or gross, and is largely incompatible with desirable automatic operation.

SUMMARY OF THE INVENTION

According to the invention a method and means are provided in a liquid chromatographic system for testing samples drawn into the system for bubble inclusion. According to the method, a liquid sample is withdrawn into a sample conduit. A volume including the sample is sealed to provide an enclosed volume. The change in pressure resulting from a change in the enclosed volume is sensed to ascertain whether there may be a bubble inclusion in the sample. A combination according to the invention may include the sample conduit, a pressure sensor coupled to it, means for entering the sample into the conduit, means for changing the volume of the enclosed space to change the pressure applied to the sample, whereby the change in pressure sensed by the sensor resulting from the volume change affords an indication of bubble inclusion in the sample. A suitable pressure sensor may be a Bourdon sensor, such as described in U.S. Pat. No. 3,855,129 to Abrahams et al, issued Dec. 17, 1974, and assigned to the assignee of this application. If desired, the change in volume may be made incrementally and the number of such changes to achieve a requisite change in pressure may be counted. If the count exceeds a predetermined count, then the change in pressure per incremental change in volume is so small as to indicate the inclusion or possible inclusion of a bubble.

BRIEF DESCRIPTION OF THE DRAWINGS

The various objects, advantages, novel features of the invention will be more fully apparent from the following description when read in connection with the accompanying drawings in which:

FIG. 5 is a schematic diagram of a syringe and needle assembly illustrated as a block in FIG. 4;

FIG. 5A is a partial schematic diagram useful in explaining control of a stepping motor;

FIG. 6 comprising FIGS. 6A and 6B is a longitudinal sectional view illustrating the drive and control arrangements for part of the syringe and needle assembly of FIG. 4;

FIG. 7 is a longitudinal sectional view illustrating a carousel drive assembly of FIG. 4;

FIG. 8 is a sectional view of a bottle verify shown as a block in FIG. 4;

DETAILED DESCRIPTION

The Valve Apparatus

Figure 1:
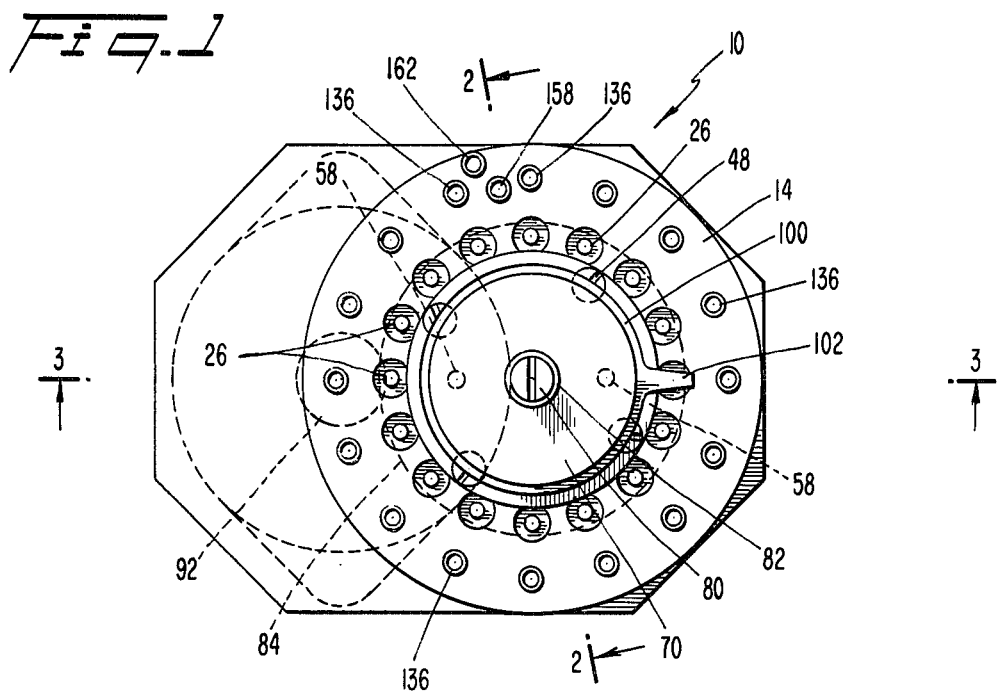
FIG. 1 is a top view of an air valve apparatus employed in the system hereinafter described, in which the invention is embodied.
Figure 2:
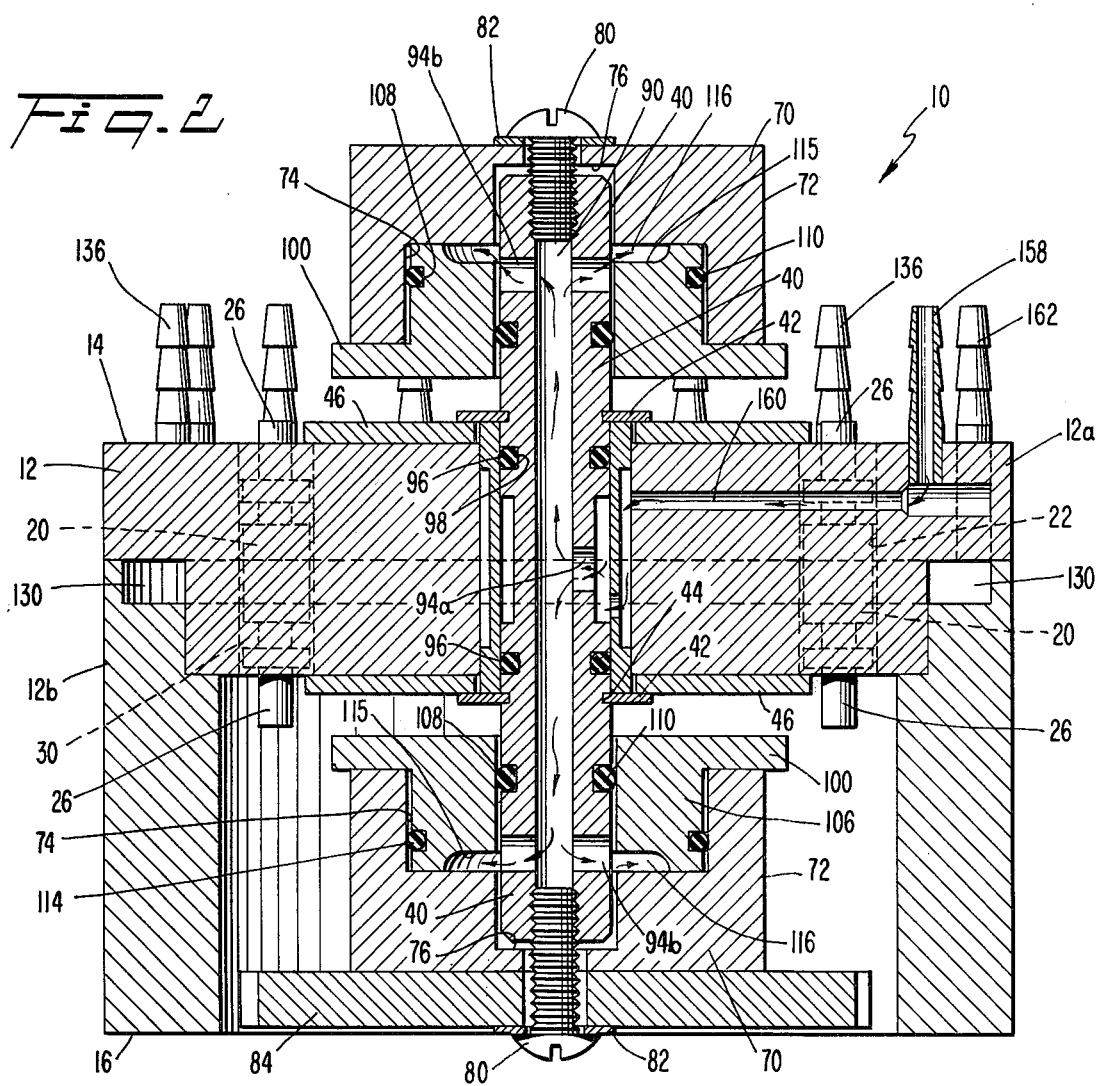
FIG. 2 is a longitudinal sectional view along the lines 2—2 of FIG. 1.
Figure 3:
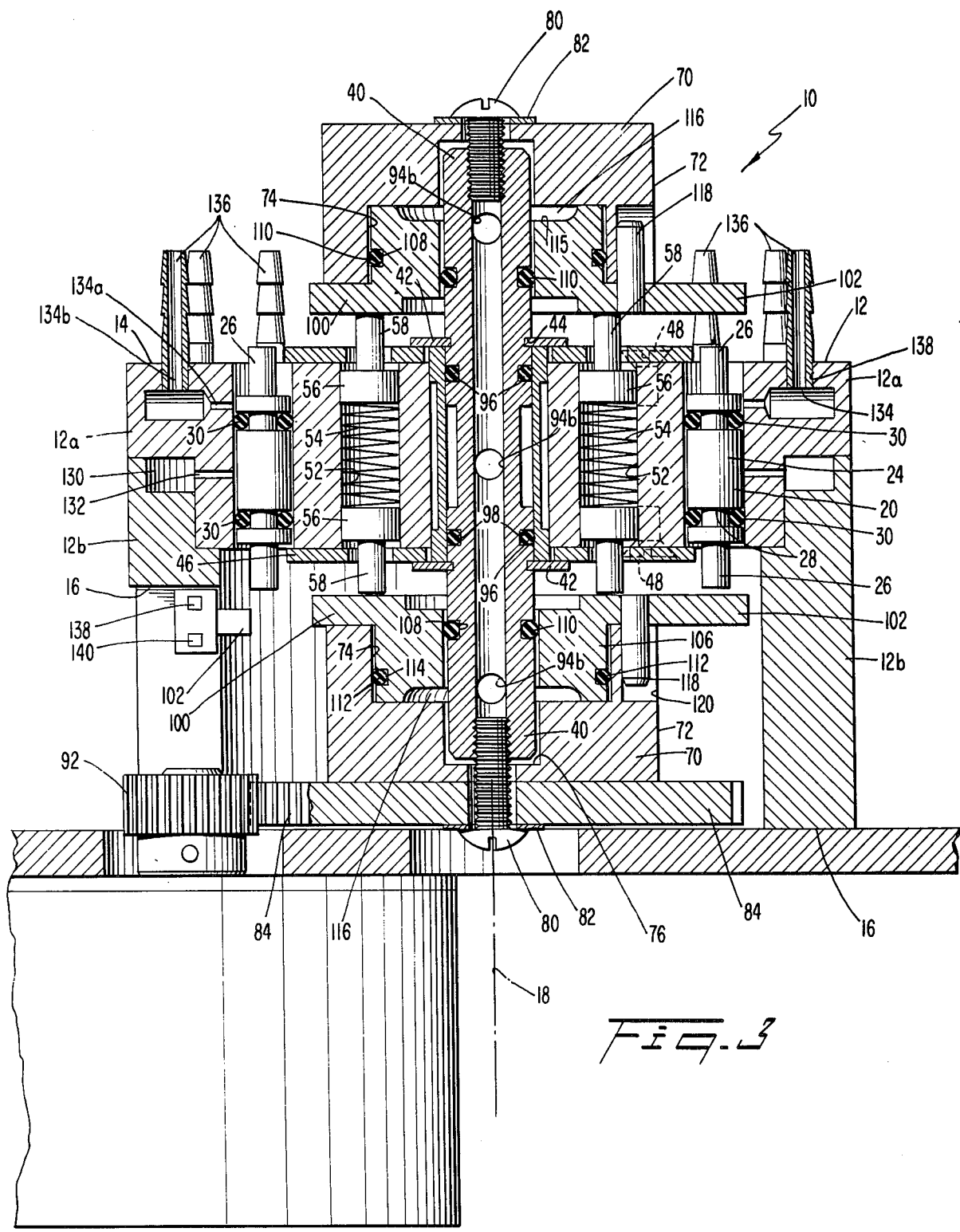
FIG. 3 is a longitudinal sectional view along the lines 3—3 of FIG. 1.

Referring to FIGS. 1, 2, and 3, a preferred embodiment of a valve apparatus 10 according to the invention comprises a generally cylindrical structure 12 having opposite, outwardly facing faces 14 and 16. The apparatus may be called RAD, an acronym for rapid air delivery. For convenience, the structure is described in the orientation shown, although it may be oriented in any way. Thus we call the faces 14 and 16 upper and lower respectively. In the structure 12, at equal angular intervals about the axis 18, are located spaces for sixteen digital valves 20, of which only fifteen spaces are used. These are referred to as digital valves because they have two positions which may be considered as on-off positions and therefore correspond to the binary digits 1 and 0. Each valve 20 is located in a bore 22 which extends through from face to face of the structure 12. Within the bore 22 is a valve core 24, cylindrical in form and having two positioning pins 26 extending from opposite sides of the core 24. The cylindrical core fits comfortably into the bore 22 with a clearance of about 17 thousandths (0.017) inch. Each core 24 and the extending pins are symmetrical about a center plane normal to the axis of each cylindrical core 24. Equidistant from this central plane are two annular slots 28 about each core 24 in which are seated O-rings 30 made of polyethylene or the like. The O-rings 30 are sized to fill the annular slots 28 and extend with adequate pressure against the wall of the bore 22 to provide a pneumatic seal between the core 24 and the wall of the bore 22.

A pair of annular retaining rings 46 are held against the respective faces 14, 16 by screws 48 threaded into the respective faces, and the C-rings 42 are flush against the outer faces 14, 16 of the retaining rings 46. A spindle 40 is retained in the structure 12 by C-rings 42 against retaining ring 46 which are engaged in annular slots 44 in the spindle 40 to leave the spindle free for rotation, but preventing its axial movement.

A pair of axial bores 52 in the structure 12 at a radial distance from the axis 18 substantially less than the radial distance of the valve bores 22 enclose as resilient means a pair of coil springs 54 each end of which is received in cups 56 from which extend thrust pins 58. The cups 56 are retained at their edges by the retaining rings 46 and the coil springs 54 are thus held under compression.

Mounted at each end of the spindle 40 are a pair of cylinder blocks 70. Each cylinder block 70 has an outer cylindrical surface 72 and an inner cylinder 74 coaxial with the cylindrical structure 12. Each cylinder 74 has a centrally located further recess 76 within which is received one end of the spindle 40. Coaxial with the cylinder block 70, the cylinder 74, and the recess 76, at each end a bolt 80 engages a washer 82 and is threaded coaxially into the axial end of the spindle 40. At one end only, the bolt 80 also holds in place a drive gear 84 having gear teeth driven by a pinion gear 92, thus providing for the drive gear to rotationally drive one of the cylinder blocks 70 axially, as shown, the lower one. The drive gear 84 in turn may be driven by a pinion gear 92 in a fashion to be further described hereinafter.

A pair of pawl plates 100, each annular in shape, carry radially extending pawls 102. Each pawl plate 100 is urged axially against the cylinder block 70 by the action of the thrust pins 58, and therefore normally rests against the inwardly axial end wall of the cylinder 74.

A pair of pistons 106, annular in shape, are coaxially mounted respectively about the spindle 40 and within the cylinders 74 so that each piston may freely move in the axial direction. A pair of annular cylinder seal slots 108 in the spindle 40 carry a pair of O-rings 110 which provide a pneumatic seal between the spindle 40 and the piston 106. A pair of annular piston seal slots 112 carry O-rings 114 providing piston seals between the piston 106 and the walls of cylinder 74. Each piston 106 at its surface remote from the cylindrical structure 12 has a hollow seat 115 forming with the cylinder 74 a cylinder chamber 116.

A pair of drive pins 118 may be press fit into the pawl plates 100 and slide inside slots 120 in cylinder blocks 70. Thus when the lower pawl plate 70 is driven by the drive gear 84 to rotate about the axis 18, the spindle 40 held by the lower bolt 80 is driven, and, also because of bolts 80, the cylinder blocks 70 are driven at the same time, the structure 12 remaining stationary. The pins 118 held in slots 120 assure that the pawl plate 100 and the pawls 102 are also driven rotationally and remain always at the same angular relation with respect to each other about the axis 18. If desired, a screw (not shown) may be threaded radially into each cylinder block 70 and entered or set into an accurately located indentation in spindle 40 as a set screw thus to insure a more exact angular orientation of the pawls 102. Thus, the pawls 102 are driven to rotate together and may be impelled axially toward each other and return without losing their relative angular orientation.

An annular plenum chamber 130 is provided in the cylindrical structure 12, in this instance approximately midway between the upper and lower faces 14 and 16. From the chamber 130, radially inward passageways 132 form separate inlets for the respective digital valves 20. The inlet passageways 132 enter approximately midway between the faces 14, 16, and the bore 22 for the valves. The exits or outlet passageways 134 (comprising horizontal parts 134a and vertical parts 134b) from the valves 20 may lead from each bore 22 from nearer the face 14, the upper face, at such a point that when the pawl 102 strikes the lower pin 26 to raise the core 24, and the lower edge of the pin 26 is substantially flush with the lower surface of the retaining ring 46, then the O-rings 30 of that valve will lie above and below respectively the exit passageways 134 and the inlet or entrance passageways 132. In the other, lower (as viewed in FIG. 1) position of the valve core 24, the upper one of the O-rings 30 is below the upper, exit passageway 134. Outlet ports 136 are provided which lead upwardly as viewed in FIG. 3 beyond the surface 14 and each communicates with the vertical portion 134b of the exit passageway 134 which communicates in turn with the horizontal portion 134a of the passageway 134.

In forming they cylindrical structure 12, it may be made of two parts, an upper part 12a and a lower part 12b. The different passageways may then conveniently be drilled or machined or cast in the two parts 12a and 12b before they are assembled. They may thereafter be assembled by a press fit, or they may be soldered or brazed. It has been found most convenient, however, to join the two parts by so-called room temperature vulcanized rubber. The plenum chamber 130 is formed of the space between two machined parts after their joining. The upward leading portion 134b of each exit passageway 134 is drilled to communicate with the horizontal portion 134a of its respective exit passageway 134. The horizontal portion 134a may be drilled from the outer, cylindrical surface of the upper part 12a of the structure 12 and the outer portion thereafter plugged in any suitable way.

To provide a supply for the plenum chamber 130, instead of the sixteenth valve, the outlet for that position is used as an inlet port 162 (see FIG. 2) for the plenum chamber 130. For this purpose, the horizontal bore portion 134a is not drilled, the vertical portion 134b is drilled down farther to reach communication with the plenum chamber 130 and thus affords entry of air from that port 162 to the plenum chamber 130.

One of the digital valves 20 may be designated as the first valve and adjacent the position of the lower pawl 102 which at that point could actuate the valve core 24 to the open position by driving its lower pin 26 upward is a small infrared emitter 138. The emitter 138 (see also FIG. 4) is positioned to bounce the infrared radiation off the end of the pawl 102 when it is in the zero position. (Ground connections are omitted.) The reflected infrared emission is picked up or detected by an infrared detector 140 conveniently in the same package as the emitter 138. The infrared emission from emitter 138 is actuated in response to a pulse from a microcomputer 200. A coincidence circuit 142 responds to the coincidence of the pulse from the microcomputer which energizes the infrared emitter 138 and the return pulse from the infrared detector 140, an output from a coincidence detector 142 thereby confirming by a pulse returned to the microcomputer that the lower pawl 102 is in the zero position.

A stepping motor 144 is conveniently mounted adjacent the valve apparatus 10 on one side of the zero detector 140. The stepping motor 144 is coupled by a suitable gear, such as the pinion gear 92 shown in FIG. 3, to the drive 84. The stepping motor 144 is bidirectional and intended to drive the drive gear 84 in a clockwise or counterclockwise direction as desired.

The stepping motor 144 makes a complete rotation on its own shaft in 48 steps of $7\frac{1}{2}°$, but is geared 4 to 1 to the drive gear 84 whereby it requires 192 steps of the stepping motor to rotate the drive gear 84 one complete revolution. Therefore, one motor step results in a 1.875° turn of the drive gear 84 and spindle 40. The sixteen lower pawls 102 are spaced from each other, center line to center line, at 22.5° intervals, as are the upper pawls 102. The upper pawls, considering rotation in a clockwise direction as viewed in FIG. 1 from above, leads the lower pawl by 11.25°.

A longitudinal bore 90 is provided through the spindle 40. A central aperture 94a and upper and lower apertures 94b and 94c are drilled transversely to communicate with the central bore 90. The upper and lower apertures 94b are positioned near the end of the spindle 40, so that they communicate with the cylinder chambers 116 either directly or through the play between the spindle 40 cylindrical walls and the surrounding piston walls 106. An inlet port 158 leads to the central bore 90 through a horizontal bore 160.

The output board of the microcomputer 200 may include amplifiers and control of additional voltage level sources as needed. An output of the microcomputer 200 is applied by a line 150 to the solenoid 229 of a normally closed air valve 228 having its pneumatic output connected by air line 156 to the port 158 for the bore 160 and receiving its pneumatic input, say, air under pressure, from a source or line of pressurized pneumatic fluid 154.

A solenoid 227 is actuated by current from the microcomputer 200 via a line 251 that opens a main air valve 226. Air from the main air valve 226 is applied to the port 162 so that the plenum chamber 130 is also pressurized.

A suitable air or nitrogen supply 220 is the ultimate source of pneumatic pressure and it may be any suitable pump or a cylinder such as are commercially available. An accumulator 222, which may take the form of a small tank, may receive the supply of compressed air (we will assume hereinafter that the supply of pneumatic medium is air). A pressure regulator 224 of any standard type passes the air to the line 154, which may be considered the main air supply and passes thence to the two pneumatic valves 226 and 228. A pressure switch 230 is connected to the outlet of the air accumulator 222. The switch 230 closes when the air pressure falls below a certain amount, say 23 psig. Closure is sensed by the microcomputer 200 in a manner hereinafter described.

There are 15 outlet ports 136 from which the pneumatic medium, the air, is conducted through suitable channels to various pneumatically driven devices to be described hereinafter. The various valves are designated RAD 1 through RAD 15, but only RAD 1 through RAD 13 are employed, the remaining two being held in reserve for possible other use.

In operation, we may assume that the microcomputer 200 has ascertained the zero position of the lower pawl 102. The microcomputer also controls a stepping circuit 148 and in response to a program will direct the stepping circuit 148 to emit pulses to control the motor 144 to step at 7½° steps, namely at 45° for the motor shaft and 11¼° steps for the drive gear 84. The microcomputer stores the current pawl positions in memory. By this means under the direction of the microcomputer program, the upper or lower pawl 102 may be brought over or under, as desired, the pin 26 of a selected valve 20. A suitable control pulse from the microcomputer may then be applied via line 150 to the normally closed air valve 228. The pulse on line 150 opens the normally closed valve 228 to pass air from the air supply 154 via an air line 156 to the inlet port 158 and thence through the passageway 160 and into the longitudinal bore 190 to actuate the pistons 106 and close both pawls 102 toward each other. Upon conclusion of the pulse from the pulse amplifier 150, the normally closed valve 228 returns to its closed position.

The air valve 228, like the air valve 226 is a valve usually used as a valve with one inlet port normally connected to an outlet port and when the solenoid is actuated, connected to a second outlet port. When the current ceases, the inlet is again connected to the one outlet port and disconnected from the second outlet port. In the present use, one former outlet port is used as an inlet port, hence the valve is normally closed. The other, second outlet port is left open to atmosphere. The usual inlet now is an outlet. Hence the new outlet is always relieved to atmosphere when the valve is in normally closed state, and is connected to the inlet port when the solenoid is actuated. Valves such as just described are readily available. Thus the valve 202 may be a model MRD002 manufactured by the Skinner Corporation. Upon relief of this pressure, and as the pressure at the port 158 declines toward atmospheric pressure, the springs 54 operate to return the pawl plates 100 and the pawls 102 to their normal distal positions.

The System

Figure 4:
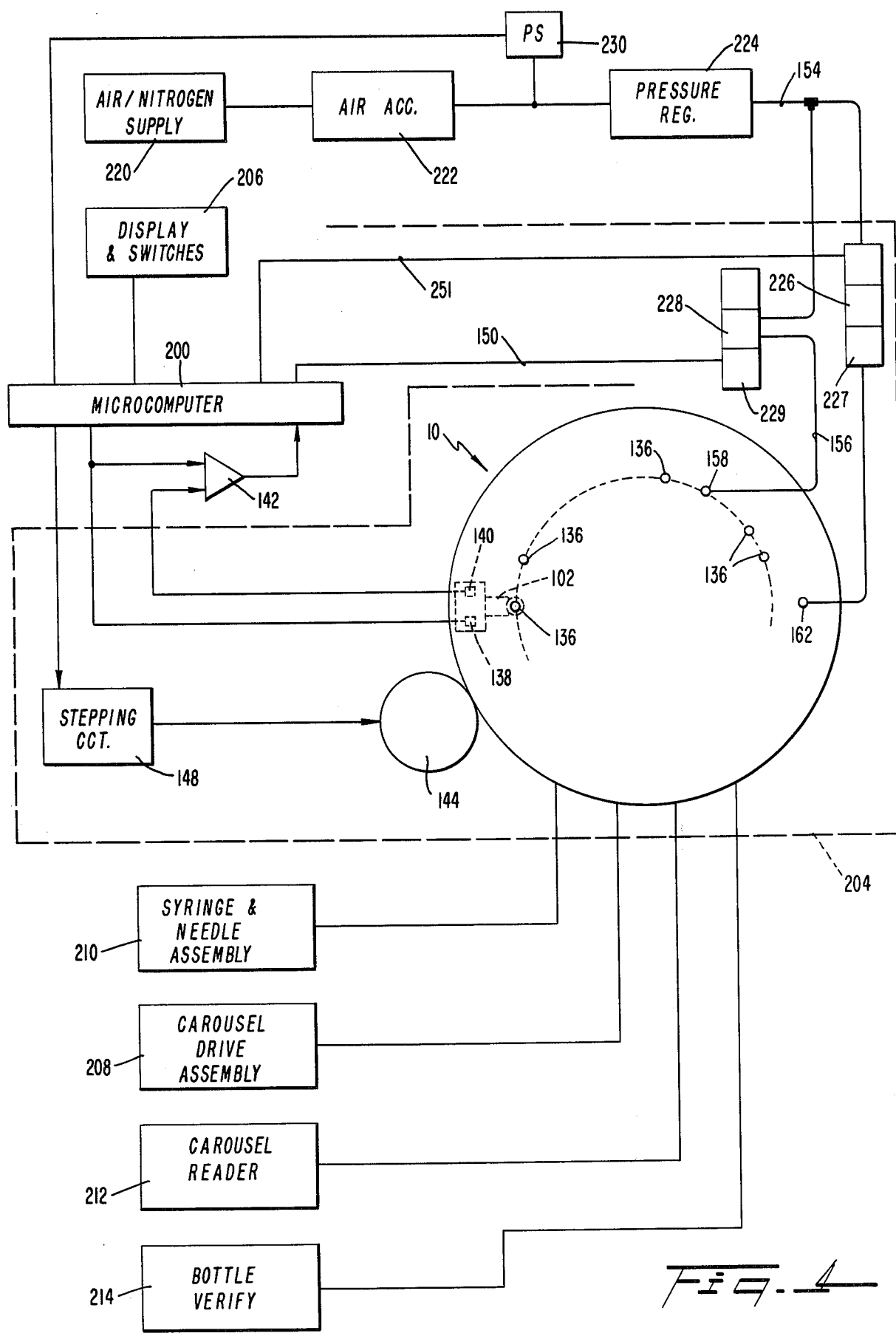
FIG. 4 is a block schematic diagram of the chromatographic system in which the invention is embodied.

Referring to FIG. 4 there is illustrated for preliminary general discussion in block diagram form a system for the automatic insertion of a sample and for the separation in a chromatographic column of the sample. The system is under control of the microcomputer 200 which is connected by suitable signals to, and receives signals from the so-called RAD assembly 204, a display and manual switches 206, a carousel drive assembly 208, a syringe and needle assembly 210, a carousel reader 212, and a bottle verify device 214.

The RAD assembly 204 is connected pneumatically as described hereinafter to a carousel drive assembly 208, to the syringe and needle assembly 210, to the carousel reader 212, to the bottle verify device 214, and to certain high and low pressure liquid valves described hereinafter.

The display and switches 206 permit the operator to insert the sequence of desired events. The air/nitrogen supply 220 may be a standard cylinder of compressed air or nitrogen (we may assume air) feeding an air accumulator 222, which may be a simple one-quart enclosure or tank. The normally open pressure switch 230 connected to the microcomputer 200 closes when pressure falls too low for operation and then the microcomputer inhibits further operation. Pressure regulator 224 may be any standard pressure controller. The regulator 224 leads to an air line, the supply line 154, which is applied to the normally closed valve 226 described above. The outlet for valve 226 leads to plenum input port 162. Line 154 branches to lead to the input of valve 228 the output of which leads to line 156 and thence to pawl actuation input port 158. The microcomputer controls sequencing of the valves RAD 1, RAD 2, etc., by connection to the solenoids 227 and 229 of valves 226 and 228.

When operation is initiated under control of the microcomputer, the RAD assembly 204 is driven to an initial condition. Thereafter, under control of the microcomputer 200 the RAD assembly 204 pneumatically prepares the syringe assembly 210 for an initial condition by opening or closing appropriate RAD valves. Then still under control of the microcomputer, the RAD assembly pneumatically actuates the carousel drive assembly 208 to pick up a carousel. The carousel carries the samples in vials. It is driven or stepped under control of the microcomputer so that the syringe and needle assembly 210 which pneumatically drives a connected hollow needle into successive samples and by action of a syringe picks up and inserts the liquid samples into a sample conduit or sample loop in the syringe and needle assembly 210. A space including the sample in the sample loop is sealed. A pressure sensor is connected or coupled to this space. Now the syringe of the syringe and needle assembly 210 is stepped by increments. The number of syringe drive increments required to cause the pressure sensor coupled to the sample conduit in the syringe and needle assembly 210 to indicate a pressure equal to or in excess of 30 (thirty) psig is counted. A count greater than a predetermined count held in computer memory indicates a possible bubble inclusion in the space. Then the computer causes the test process to be repeated. If a repetition yields similar results, then the effort to inject that sample may be aborted. Such a result indicates compressibility compatible with bubble inclusion and not compatible with the lesser compressibility of all liquid in the space. If a run should be aborted, then the syringe and needle assembly 210 under control of the microcomputer disposes of the unsatisfactory sample so that the sample conduit is again filled with eluent before it withdraws another sample from the carousel drive assembly 208, the carousel of which is stepped to present a succeeding sample for trial.

Further details of the system and its operation will be explained in the description which follows.

Syringe and Needle Assembly

Referring now to FIG. 5 there is illustrated the syringe and needle assembly 210 from which it will be apparent that the chromatographic system here described employs the principles of U.S. Pat. No. 3,916,692, issued Nov. 4, 1975, to Abrahams et al and assigned to the assignee of the present application. A primary conduit 234 receives liquid eluent or solvent from a pump 236 which draws the eluent from an eluent reservoir 238. The pump 236 is a displacement type pump. The line 233 from the pump 236 passes to a normally open high pressure liquid valve 240. The valve 240, under control of RAD 1, contains in its casing a junction one output from which continues to a liquid primary conduit 234. The other output from the junction leads to the normally open high pressure liquid valve 240, the output of which leads to a line 244 which leads to a second junction in the casing of a second normally open high pressure liquid valve 246. The valve 246 is under control of RAD 2. The one branch from the second junction in the casing for valve 246 leads through a Bourdon tube 360 to a sample conduit 248, and the other branch leads to the valve 246. The output of valve 246 goes to a line 247. The line 247 leads to a junction 265 having three branches. One branch of the three leads to the normally closed low pressure liquid valve 266. A second branch of the three leads to the output from a syringe 264 actuated by a syringe drive 262. The third branch leads to a relief valve 268 set at 125 psig. The side of the relief valve remote from the three-way junction is connected to the output of the low pressure valve 266 and also to a drain.

The sample conduit or loop 248, which may be considered to include the Bourdon tube 360, is continued to include a coil 249 stylistically indicated, which physically may be in an injection valve 242, which is connected to the bore of a bored needle 250 which has an opening 252 near its end and communicating with the bore.

A normally closed, low pressure liquid valve 254 is under the control of RAD 4. The liquid inlet to valve 254 is any suitable solvent such as solvent from the reservoir 238. The output of the solvent valve 254 is applied to a needle washer 256 associated with the injection valve 242 and will be described more fully hereinafter in connection with FIG. 6. A normally closed low pressure liquid valve 258 receives drainage from the needle washer 256 and is under control of RAD 5. The outlet from drain valve 258 may go to any suitable drain, which may be the drain from the outlet of the low pressure liquid valve 266.

The syringe drive 262 is under control of the microcomputer 200. The manner in which this control is exercised will be clear from FIG. 5A. There are provided in a control circuit 298 for a stepping motor (not shown) three flip-flops, a direction flip-flop 300, a step flip-flop 302, and a power flip-flop 304. The microcomputer clock of one microsecond is divided down to provide two millisecond pulses. The desired number of two millisecond pulses is entered in a register as a result of the program and that number is now applied to the control circuit to control the number of pulses applied to the phase windings of the stepping motor, to conform to the number of steps desired. The step flip-flop 302 is set or reset. When the step flip-flop is set at the beginning of one of the two millisecond pulses coming from the microcomputer, the stepping currents are initiated. They last as long as the number of two millisecond pulses from the microcomputer are programmed. The power flip-flop 304 when set provides a high level of 5 volts to a coincidence gate 306 which permits passages of a 24 volt level, the output of which is applied as one input for power amplifier gates 308A, 308B, 308C, and 308D, the outputs of which are applied to the respective phases A, B, C, D, of the stepping motor. The phasing of the gates (not shown) is understood in the art, successive pulses being delayed and overlapped in proper sequence. In operation, if the stepping motor is to be stepped, a desired number of steps, the direction flip-flop is set or reset in accordance with the direction desired so that its output controls the sequencing of the phases in the proper sequence to rotate clockwise or counterclockwise, in accordance with the program. Next, the power flip-flop is set in accordance with the program immediately before, for example, a microsecond or two before, the initiation of the two millisecond pulses. Accordingly, in operation, the desired number of steps is supplied from the program to supply the requisite number of two millisecond pulses to drive the stepping motor in the direction in accordance with the state of the direction flip-flop 300. Upon completion of the desired number of millisecond pulses, the step flip-flop is returned to its reset condition, and the power flip-flop 304 is also returned to its reset condition thereby removing the conditioning inputs from the various coincidence phase amplifiers 308. The shaft of the stepping motor is connected to a screw which turns to advance to retract a threaded bolt connected to the syringe plunger. The desired number of steps will then have stepped the stepping motor to advance or retract the syringe to displace the plunger by a desired volume. Such control of the stepping motor and the syringe head is known.

The high pressure liquid valve 246 closes in response to pneumatic pressure from the valve RAD 2. The normally closed low pressure liquid valve 266 opens in response to pneumatic pressure from RAD 3. If the pressure at the junction 265 exceeds 125 psig, for which the check valve is set, the check valve 268 will open and release to the drain. As will appear more fully hereinafter, the syringe drive may exert a high pressure upon the output of the syringe 264 and the setting of the check valve prevents serious damage to the syringe or possibly other parts.

The Bourdon tube 360 in its originally convoluted shape partially obstructs light from a source 358. The source 358 is arranged with respect to the Bourdon tube 360 and a light sensitive element 362 in such a way that as increased pressure in the line 248 causes the Bourdon 360 to open or straighten, the tube interrupts a greater amount of light from the source 358. The light sensitive element 362, which may be a photoemitter or a suitable photoresistive element in appropriate circuit conveys an output to an analogue-to-digital converter 364. The digital output from the analogue-to-digital converter 364 is conveyed to a suitable register in the microcomputer 200.

Injector Valve Assembly

Figure 6A:
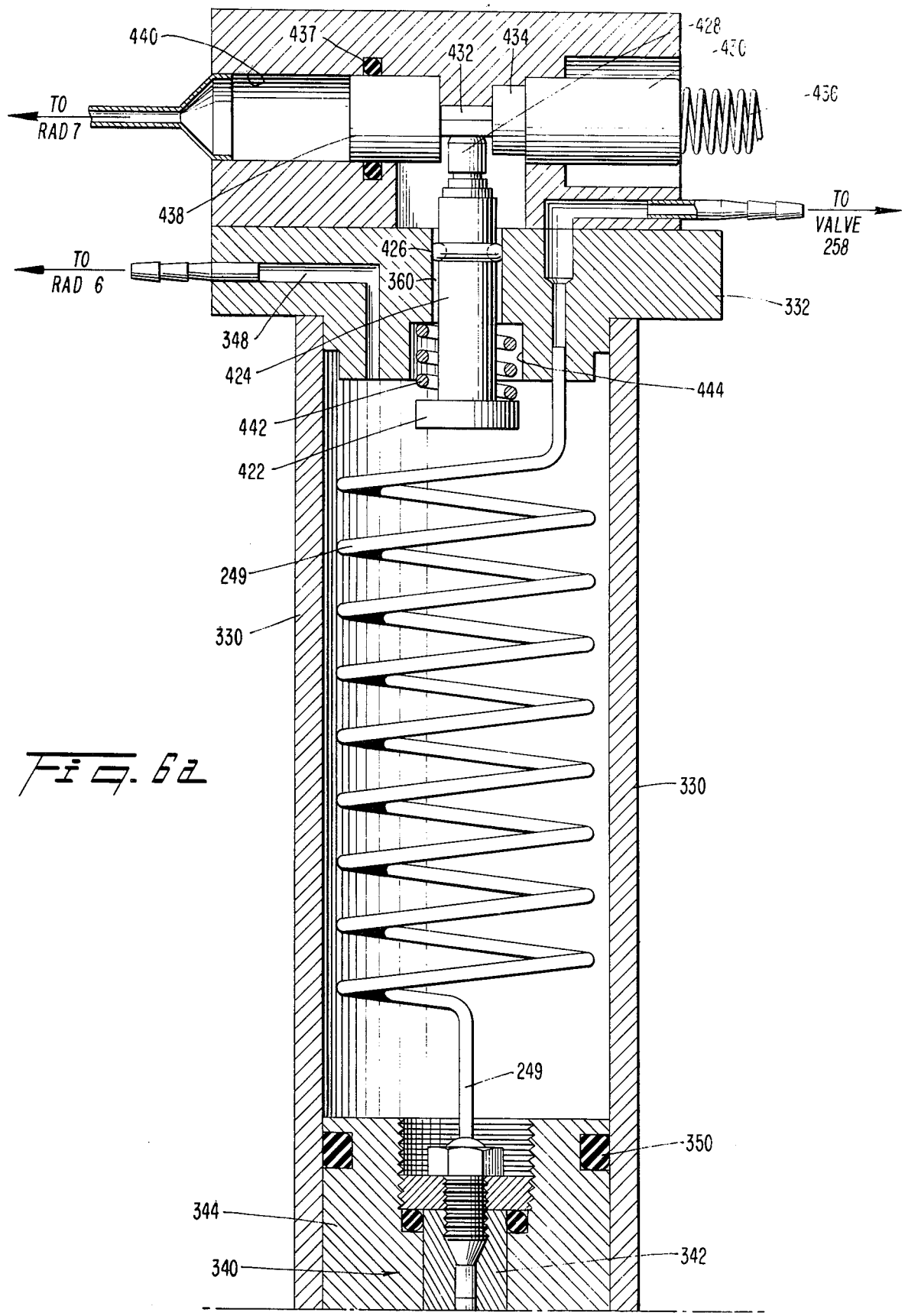

Referring now to FIG. 6, comprising FIGS. 6A and 6B, the injector valve assembly 242 comprises a number of connections to various conduits, substantially as shown and described in the co-pending application of David R. Friswell, Ser. No. 772,145, filed Feb. 25, 1977, for "Sample Injection with Automatic Cleaning of Sample Conduit". Thus, pump 236 supplies carrier solvent or eluent to primary conduit 234 which is connected via conduit 312 into the injector valve assembly 242 and an outlet conduit 314 leads to the chromatographic column, as indicated. To do this, the liquid proceeds through needle-valving block 320.

Block 320 comprises an inlet port 322 and an outlet port 324 communicating with conduits 312 and 314, respectively. The needle 250, mentioned above, is a modified hypodermic needle which has an internal bore 251 and is adapted for reciprocating vertical movement in block 320 through a central opening 361. There is an annular space 325 about the needle around which fluid can flow from conduit 322 to 324. When the needle 250 is raised the lower portion thereof, i.e. portion 327 is a plug means which effectively seals the fluid with a lower seal 372 in central opening 361. There is also an upper seal 371 in opening 361 to seal the needle.

In the first mode of operation, the valve 240 is closed. The liquid eluent passes through primary conduit 234 through the annular space 325, and directly on to the column. Upper and lower seals 371 and 372 prevent liquid loss around needle 250.

When the needle 326 is raised so that outlet opening 252 is in register with the annular space 325, the bottom portion 327 of the needle forms a seal with lower seal 372, the portion of the needle immediately above the opening 327 seals with the upper seal 371, and the sample in the needle is forced out the port 324 together with some of the eluent flowing around the needle 250 at the annular space 325. The resistance to liquid flow in the conduit 234, as indicated by R, is increased by the small diameter of conduit 234 relative to that of Bourdon tube 360, conduit 248, coil 249 and the needle bore 251, so that the major flow is through the sample loop comprising conduit 248 and coil 249, as explained in the above-mentioned Abrahams et al patent. Hence, the sample is forced out quickly.

The needle 250 is connected to the coiled conduit 249 by means 340 comprising a steel insert block 342 which, in turn, is carried in an aluminum piston 344. Piston 344 is air operated. The piston 344 moves in a cylindrical housing 330 closed at the top by a top housing plate 332 and at the bottom by a lower housing plate 334. Air to raise the piston 344 (and, of course, needle 250 connected thereto) enters from an air conduit 346 in housing 330 just above lower block 334 from RAD 8 of the pneumatic valve device 10. Air to lower the piston 344 enters from an air conduit 348 in top plate 334 from RAD 6 of device 10. The piston 344 is provided with upper and lower lip seals at 350 and 352 respectively. The upper part of the injection valve 242 is modified from the arrangement in the Friswell application, as will appear. Connection means 340 comprises ferrules on each of needle 250 and sample conduit 249. These form a butt connection utilizing fittings already well known in the chromatography art.

The seal means provided by upper and lower seals 371 and 372 are able to handle pressure to 5000–6000 psig and are able to do so for a prolonged period of time without replacement. For this purpose, these sleeves are formed of a fluorocarbon-based material. It is desirable that the fluorocarbon be reinforced; otherwise shredding or peeling of the seal may result. Advantageously, the material will have tensile and compressive strengths exceeding 1600 and 1200 psi respectively. A suitable material is well known in the art and sold under the trade designation RULON J by Dixon Corporation or that sold as D205 by Patriot Plastics and Supply Inc., Waltham, Mass. Upper and lower stress rings 373 and 374 respectively may be separate pieces as illustrated. In the case of the rings nearer the ports 322 and 324, it may be desirable to fabricate the stressing rings into block 320.

The sleeve 371 or 372 may be formed of a reinforced resin. This material has superior functional characteristics when compared to most reinforced halogenated polymer resins. It is also characterized by a minimum tensile strength of 2000 psi and a compressive strength of about 1430 psi. The stressing ring 373 or 374 may comprise a sleeve-deforming surface bevelled to a 90° angle.

Strain applied to sleeve 372 through rings 374 cause the seal to tend to push out thus tending to seal against needle 326. This pressure is achieved as the result of compression between a washer housing 388 wherein an extension 390 is threaded into block 320 to bear on the bottom-most seal ring 374 which, in turn, pushes the lower seal 372 against a portion 392 of block 320. Similarly, the uppermost seal 371 is compressed downwardly by a threaded section 394 which, like extension 390 is arranged concentrically with needle 26.

In liquid chromatographic procedures, there is usually no problem in cleaning the interior of sampling needle 250. After a sample has been sucked into needle 250 by suction of syringe 264, and the needle 250 has been pneumatically raised to its proper discharge point, i.e. with needle opening 251 facing annular space 325, then valve 246 is closed, valve 240 is opened, most of the solvent flow goes through branches 244, sample conduit 248, and coil 249. This flow not only sweeps the sample into the chromatographic column, but it also continues for a sufficient time thereafter to assure that no substantial sample contamination remains in the needle 250.

The needle washer 256 shown in detail in FIG. 6B, receives at port 411 in a washer housing 388 washer solution or eluent from the outlet of washer valve 254. The vacuum source 260 is connected through the inlet to drain valve 258 to port 412. Within washer housing 388 is a bore 389 through which needle 250 moves vertically during operation of the sample injector. About bore 389 are mounted two highly porous plugs 416 and 418 of a sintered material, e.g. polypropylene, polytetrafluoroethylene, or the like. The plugs have pores of about 20 to 40 microns in size. These are separated by a spacer 420. The plugs and spacer are snug against the needle, but without constricting its vertical movement. The operation of the washer is timed by pneumatic valve RAD device 10 under control of the microcomputer 200 (1) to supply solvent to plug 418 when the needle is down by opening normally closed, low pressure liquid valve 254 in response to pressure from RAD 4 and (2) to apply a vacuum to plug 118 when the needle is up, or when needed to prevent drip, by opening normally closed, low pressure liquid valve 258 in response to pressure from RAD 5.

Washer 256, therefore, provides means via plug 416 to wet the needle while being depressed. Any excess solvent flow through the annular space within spacer 420 between spaces 416 and 418 and is distributed within lower plug 418 and carried away in an air stream pulled upwardly through plug 418 and towards vacuum source 260. This procedure avoids any dripping of solvent from the washer. Plug 418 also forms means to wipe the needle as it moves upwardly out of the sample bottle.

As thus far described, the arrangement of FIG. 6 conforms to the said Friswell application. A minor modification is made in the portion just above the upper seal 371. Just above the stress ring 373 an annular seal 376 of fairly close fit is passed over the needle 250. The outer surface of the annular seal 376 is fit tightly in a vertical extension 378 of upper stress ring 373. The external circumference of the extension 378 is fitted with an O-ring seal 380. A vent 382 to waste is entered through the needle valving block 320. This modification assures that in the event of a leak past the upper seal 371 of liquid will flow to waste or drain rather than passing higher and possibly entering the pneumatic line to RAD 8.

A second and greater modification is made in the arrangement at the top starting with the top housing plate 332. A stop head 422 is formed at the lower end of a stop bar 424. The bar 424 is sealed pneumatically by an O-ring 426 seated in an annular groove in the bar 424. The upper part of stop bar 424 is turned down to form a stop pin 428 which, in the position shown, bears against the smaller diameter portion of a cross-pin 430. The cross-pin 430 is at right angles to the stop pin 428 and has two different diameter stop sections, a smaller diameter stop section 432 and a larger diameter stop section 434. The cross-pin 430 may be translated horizontally to two positions. In the first of these positions to which cross-pin 430 is urged by a compression spring 436, the larger diameter stop section 434 opposes the stop pin 428. In the other position, to which cross-pin 430 may be urged by air pressure fed from RAD 7 of the valve device 10, to overcome the force of the spring 436, the smaller diameter stop section 432 opposes the stop pin 428. A seal 437 by an O-ring forms with one end portion of the cross-pin 430 a piston 438 in a cylinder chamber 440 in an addition to the top housing plate 332, which piston reacts to the air pressure from RAD 7. The spring 436 acts in direct opposition to thrust of the piston 438. A compression spring 442 is received in a depression 444 in top housing plate 332 and bears against the stop head 422. The force of spring 442 is overcome by the aluminum piston 344 when driven up by air pressure from conduit 348 received from RAD 8.

Consider a cycle of events which may begin with the cross-pin under influence of the spring 436 located at the left (rather than at the right as shown in FIG. 6A) and with the aluminum piston 344 down, as shown in FIG. 6A. When the piston is driven up by opening RAD 8, since the stop pin 428 bears against the larger diameter stop section 434 of cross-pin 430, the piston 344 stops the needle 326 so that the opening 252 faces the lower seal 372, and the opening is sealed closed. Now, as will be described further hereinafter, the syringe is advanced a predetermined number of turns to perform a bubble check or test. Omitting other options for the moment, and assuming the check is negative, RAD 8 may be turned off. As there is no air pressure on either side of the piston 344 it remains in place or drops only slightly. RAD 7 is opened, air pressure is applied to cross-pin piston 438, the cross-pin is translated without friction from stop pin 428 to the right so that the smaller diameter stop section 432 faces the stop pin 428. RAD 8 is turned on and the aluminum piston 344 pushes the stop bar 424 against the force of spring 442, until the stop pin 428 bears against the smaller diameter section 432 of the cross-pin 430. In this position of the aluminum piston 344, the needle 250 has the opening 252 facing the annular space 325. The valve 246 may be closed, the valve 240 opened and the sample in the needle 326 injected or flushed into the chromatographic column. Thereafter in a typical cycle, RAD 8 is closed, the pressure against the bottom of piston 344 relieved, the spring 442 starts the piston 344 down, RAD 7 is closed and the spring 436 returns the cross-pin 430 to its initial position with larger diameter section 434 in line with the stop pin, RAD 6 is opened and the piston 344 driven down to its initial position, whereupon, if desired, RAD 6 may be closed, and the initial position held, or it may be left open to assure that piston 344 remains in position.

Carousel and Drive Assembly

The carousel and drive assembly 208 is illustrated in greater detail in the longitudinal cross-sectional view of FIG. 7. The carousel or sample carrier 470 is annular and has recesses 520 and a raised lower edge 470a to form pockets in which may be carried small sample bottles 522. On the inner circular face of carrier 470 are indentations 470b. A piston 472 operates in a double cylinder 476. The piston 472 is pneumatically sealed coaxially to an annular gear plate 478 to prevent the by-pass of pressurized air. In this case, it is the cylinder which travels vertically with respect to the piston, and may travel in either direction. The gear plate 478 carries a spur gear 480 on its outer circumference. The inner circumference of the annular plate 478 is sealed at 482 to a vertical shaft 484 which is threaded into the center of an upper plate 486 to be substantially pneumatically sealed by a seal 485 and locked in place by a lock nut 488 which allows suitable vertical adjustment as required. Two pneumatic air lines penetrate the seal 485, a cylinder down line 490 and a cylinder up line 492. The former is extended through the seal 485 down to and through the seal 485 and piston 472 being sealed also to the piston. The cylinder up line 492 passes through and is sealed to the seal 485 and terminates in the interior of shaft 484. One or more air exits 494 are provided in the shaft 484 below the gear plate 480 so that the upper part of the cylinder may be pressurized. The cylinder down line 490 is connected to the valve RAD 9 and the cylinder up line 492 is connected to the valve RAD 11.

A drive spline 498 is journalled between the upper plate 486 and a lower support block 500, and driven by a stepping motor 501 under control of the microcomputer 200. In the support block 500 are two vertically oriented cylinders 502 located diametrically oppsite each other and received therein are vertically moveable pistons 504, with pneumatic seals at 506, to which are attached piston rods 508. The piston rods 508 are threaded at 509 into a fixed mounting plate 505.

The bottom of cylinder 476 is coaxially pierced with an aperture 510 leading to a pair of diametrically opposed cylinder chambers 512 in a lower piston block 513, which is made as a part of and extending the lower end of the cylinder 476. In the chambers 512 are a pair of diametrically opposed horizontally moveable pistons 514 carrying outwardly presented detents 516. The pistons 514 are drawn toward each other by a spring 518 sufficiently tensioned normally to prevent the detents 516 from extending beyond the opposed cylinder walls of cylinder chambers 512, unless air pressure is exerted against the pistons 514 to extend the spring 518. Pistons 514 are sealed at 519.

Ports 515 lead from the vertical cylinders 502 to RAD 10 for control of the actuation of the vertical pistons 504. In the lower-most position of the pick-up cylinder chamber 512 and of the carousel cylinder 476, the gear plate 478 rests on the support block 500. A normally open microswitch 526 is located on the support block 500 to be closed when the spur gear 478 contacts this switch in the gear's lower-most position as cylinder 476 reaches or rests at the end of its down stroke.

Initially assume the carousel cylinder 476 is in the raised position, RAD 11 being open to force the cylinder up by pneumatic pressure from pneumatic line 492. Initially the carousel 470 rests on a base 524 a short distance under the raised cylinder chambers 512. Thus, the carousel 470 may be removed or rotated manually in place for insertion or removal of sample bottles 520, the recesses 520 in the carousel 470 outer periphery affording easy receipt or removal of the sample bottles 522. RAD 9 and RAD 10 may be assumed initially closed. Now under control of microcomputer 200, RAD 11 may be closed and RAD 9 opened. Thereupon the cylinder 476 is forced down. The drive spline 498 and gear 478 remain engaged. The detents 516 remain in place because as the piston moves, the air pressure in the lower cylinder chamber of cylinder 476 remains low, because the piston motion enables the air entering the lower chamber to expand. Nevertheless, when the cylinder 476 strikes block 500 and reaches the bottom of its stroke, the pressure then builds up through aperture 510 to actuate horizontal pistons 514 in opposition to the spring 518. As the pistons 514 are forced out, the detents 516 engage the indentations 470b. At the same time the microswitch 526 is closed, and the microcomputer 200, to which it is connected, sends a sensing pulse the return from which (in the same manner as for other microswitches described herein), stores in memory an indication that the cylinder 476 is adjacent the support block 500. Now the microcomputer signals RAD 10 to be opened. This applies pressure against the two vertical pistons to raise support block 500 which thereby raises the drive spline 498, spur gear 478, cylinder 476 attached and sealed thereto, lower block 513 and carousel 470 held by detents 516 in indentations 470b. The stepping motor 501 may now drive spline 498 and gear 478 to rotate the carousel as desired, and position it in a manner to be more fully described.

When the carousel is to be returned to the floor 524, RAD 10 is closed, the pressure in vertical paired cylinders 502 returns to atmospheric level, gravity causes the support block 500 and attached parts to drop. At the same time or immediately after, RAD 9 may be closed. Pressure in cylinder 476 and chamber 512 is relieved. The spring retracts the detents 516 from indentations 470b. RAD 11 may be opened to cause cylinder 476 to raise, the drive gear 478 remaining throughout engaged with spline 498. As soon as spur gear plate 480 raises from support block 500, the microswitch 526 assumes its normally open position and the microcomputer has note of this condition by lack of return signal.

Bottle Verifier

The bottle verifier, FIG. 8, comprises a normally open microswitch 448 in a housing 450 which is held by a piston 451 held retracted by a tension spring 452 in a cylinder 453 fed by air from RAD 12. The switch 450 has a feeler arm 454 which when swung closes the switch. When RAD 12 is opened in response to appropriate signals from the microcomputer 200, the switch housing 450 is thrust by action of piston 452 into position so that the feeler arm strikes any bottle top in the 48 bottle positons afforded by the carousel 470. If a bottle is present, the microswitch 450 is closed, the presence of the bottle sensed, and the information that a bottle is present in that location stored in the microcomputer memory. If a bottle is absent, the microswitch remains open, and the information that a bottle is absent in that location is stored in the microcomputer memory. A bottle absent indication will inhibit the computer 200 from directing a plunge of the needle 250, i.e. the opening of RAD 6, and assure that RAD 8 is open, so that the piston 344 is kept in an up position (see also FIG. 6). After the initial count operation to detect the bottles which may be present, the RAD 12 is closed and the housing 450 is retracted so as not to interfere with the carousel and sample bottles during further operation of the system.

Carousel Reader

Figure 9:
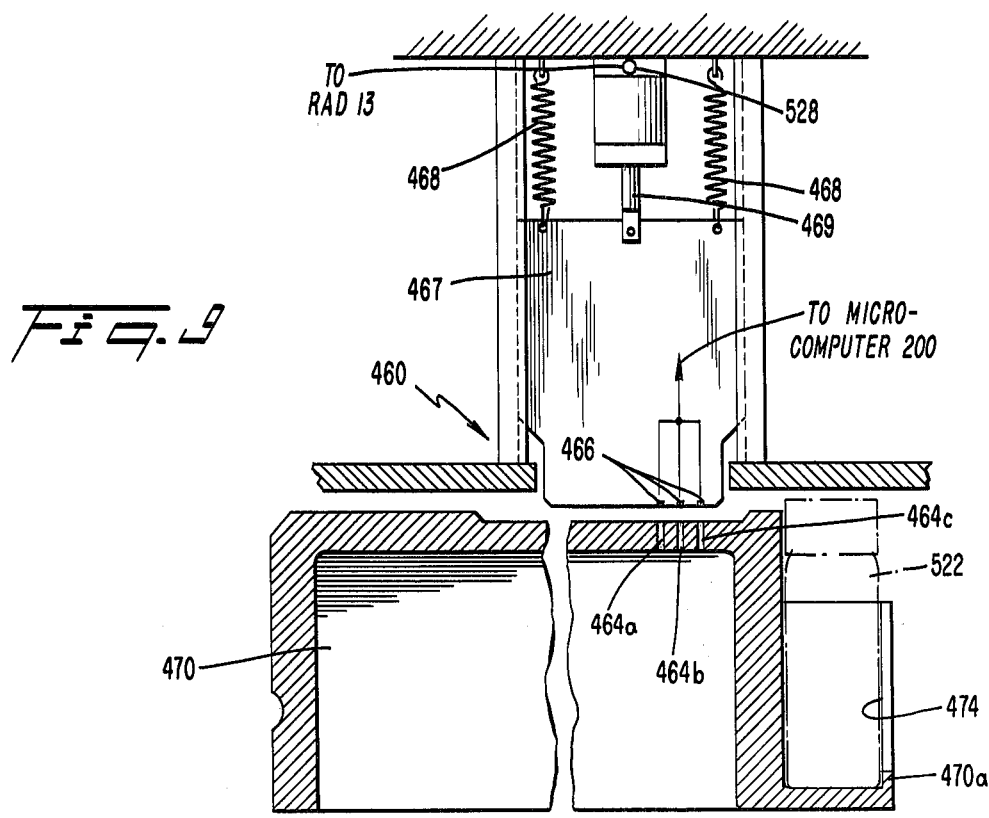
FIG. 9 is a sectional view of a carousel reader shown as a block in FIG. 4.

The carousel reader 460 (FIG. 9) contains three light detectors 466 the outputs of which are connected to the microcomputer 200. The detectors 466 are in a holder 467 which is slidably mounted to a piston 469 in a cylinder. The piston 469 is forced down by air to port 528 from RAD 13, and retracted by springs 468.

When carousel 470 is first raised, RAD 13 is opened and the holder 467 depressed to bring the detectors 466 close to and immediately over the position under which the three apertures will move. There are three LED's (light emitting diodes, not shown) in the holder 467, one for each detector. Thus, the three detectors in the holder 467 read or react separately to light from the three LED's reflected from the carousel 470 except when the holes 464 are in position marking one of the 48 locations of the carousel. Three holes mark the "one" position of the carousel. The three detectors 466 thus are depressed to a reading position. As the carousel stepping motor 510 first steps the carousel 470 successively it reaches the number one position which is recognized by the computer because of the simultaneous failure to receive signals from the three detectors indicating that all three have failed to receive reflections from the three LED's. Circuits for this purpose are well known. The computer tests for the response of the detectors at each location, or at each step of the stepping motor, and when the first position is found, that position is stored in computer memory. Thereafter as the carousel 470 is stepped, each step to each position clockwise or counterclockwise from the zero position, is added or subtracted from the first position, so that the current position of carousel 470 always stored in memory in the fashion similar to the way in which the position of the pawls of RAD device 10 is stored in memory. Nevertheless, an additional parity check is performed by means of the two outer radius holes 464b and 464c respectively. The intermediate holes 464b occur at only every other position at like radial distances, and the outer holes 464c occur at every position at like radial distances. It is, therefore, relatively simple to test whether the position from the beginning position is odd or even. The parity check is tested against the current position stored in memory and assures that the carousel drive motor 462 has not because of inertia or for some other reason passed a step or failed to make a step. When the carousel 470 is dropped, RAD 13 is closed and the reader holder 467 retracts to initial position out of the way. The LED's for detectors 466 need no longer be actuated.

The System Operation

The microcomputer may first sense whether the pressure switch 230 is closed or not. For this purpose one of the leads from the microswitch is connected to receive a pulse under control of the program. Such a pulse may come from the timing or one microsecond clock pulses of the computer and may be applied at a frequency such as every millisecond or any multiple of the clock pulse. The other lead from the normally open switch 230 may then be applied to a suitable amplifier or coincidence circuit. If the output of the amplifier or coincidence circuit responds, in other words, if the programmed pulse is passed, then the switch is closed. Consequently, the output from the amplifier or coincidence circuit may be employed with the microcomputer to exercise control as called for by the program. The applied pulses may be applied with a lesser frequency when desired, say every millisecond or half millisecond by dividing down the clock pulses, by known techniques. Similar arrangements may be used to detect closure of other switches noted herein as under control of the microcomputer.

As noted hereinbefore, the solenoids 227 and 229 of the valves 226 and 228 are respectively connected to the microcomputer so that they are under its control. For this purpose, a solenoid control output pulse at the 5 volt level from the microcomputer for each separate solenoid is applied to a coincidence circuit which receives at its other input a 24 volt supply which is adequate to actuate the solenoid. The 24 volt supply is constantly applied to the one input. The microcomputer solenoid control pulse is, of course, under control of the program in the microcomputer and may, by well known techniques, be of a suitable time duration, such as 5 milliseconds to operate these air valves. When the solenoid is not actuated, the input is closed off. At this time the output and relief passageways are connected together. As noted above, the relief passageway simply exits to the atmosphere. When the solenoid is actuated, the input passageway from the source of air under pressure is applied to the output passageway, and the relief passageway is disconnected from the other two passageways. Consequently, when the solenoid no longer receives current, the output is connected to the relief passageway and thus to atmospheric pressure. Actuating valve 228 may then be opened.

Next in initiating operation, the computer causes the stepping motor 144 to step until the microcomputer 200 has stored in its memory the first location, as noted above, which in this instance is the location at which the first digital valve 20 is positioned directly over the upper pawl 102. The digital valves 20 are numbered RAD 1 through RAD 15 in clockwise rotation viewing the RAD from above as seen in FIG. 1. Then as the stepping motor 144 steps around RAD 1 and RAD 2 are opened, RADs 3 through 7 closed, RAD 8 opened, and RADs 9 through 13. These three valves, RAD 1, RAD 2, and RAD 8 being open insure that initially the two high pressure liquid valves 240 and 246 are closed and that the needle 250 is up so that it will not interfere with insertion or withdrawal of sample bottles in the carousel 470, nor with their preliminary motion. During this initial setting of the RAD, note that main valve 226 remains closed. After this initial setting is achieved, main valve 226 is opened, and air flows to the plenum chamber 130.

Figure 10:
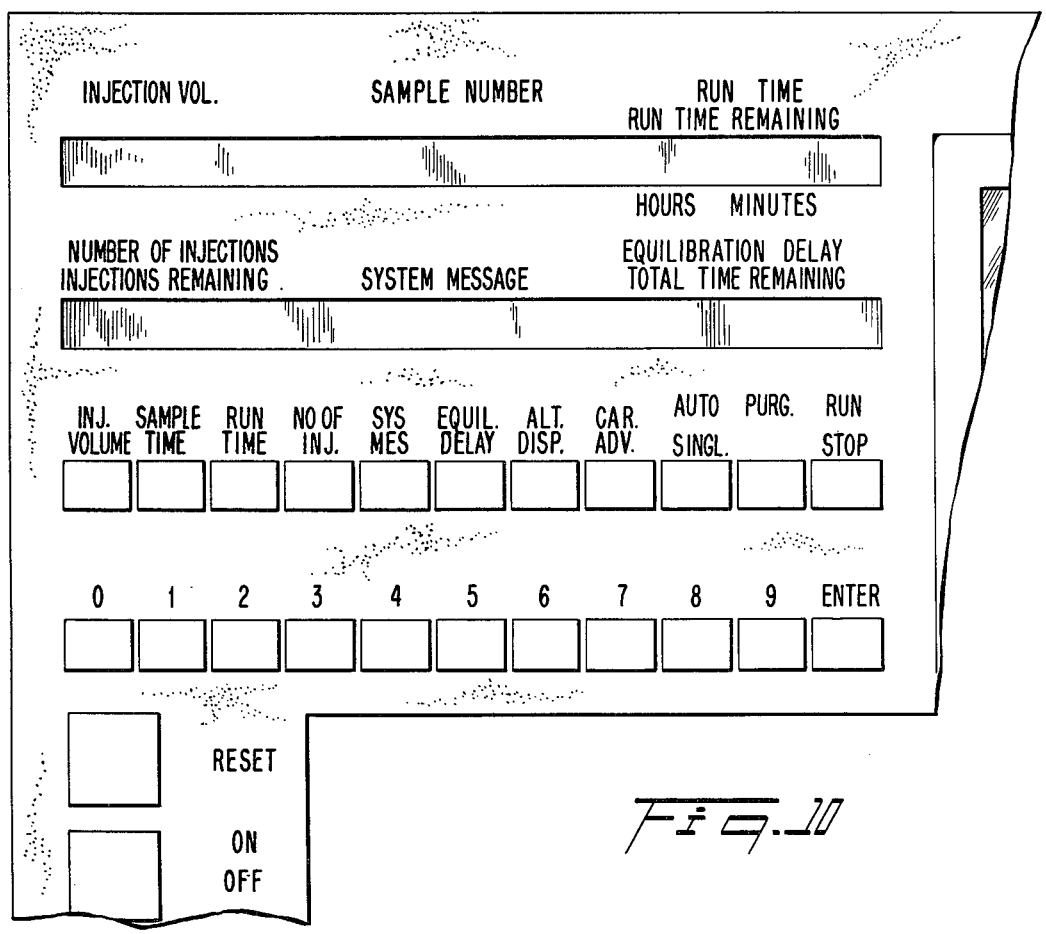
FIG. 10 is a representation of the control panel of the system useful in explaining its operation.

When the user sets the on-off switch (see FIG. 10) on the panel 550 to "on", the foregoing action takes place. Now when power is applied to the pump 236 and solvent or eluent begins to flow. Next the user loads the carousel 470 which for this purpose may be removed for easy access through a suitable opening in the panel 500. The sample bottles 522 of a known type having septum covers may be loaded, careful note being taken by the user of which samples are located in which location. The carousel may then be inserted in the opening in the control panel 500. Then the access door is closed. At this point the system is in single inject mode. First the "Sample No." key is depressed, and the sample number set out in the same manner, appearing displayed under "sample number" above, and entered. Next the user depresses the key marked "INJ VOL". He may then enter the volume in microliters, pressing successive digits in the normal way from the greatest significant digit to the least in microliters. The volume will appear an LED display by customary techniques under "Injection Volume" (upper left). The display will blink until the lever "enter" is depressed to store the information in a suitable computer register. Next the "Run Time" key is depressed showing the Run Time under "Run Time — Run Time Remaining". Run time is entered by hour and minute (not to exceed 9 hours 59 minutes). By depressing the "RUN" key a single injection will follow. The system may be placed in automatic mode by depressing the "AUTO SINGLE" key. To program a set of parameters for all injections designate sample No. "0" and enter the desired parameters. To designate exceptions to this set of parameters designate a sample number to be changed and enter the desired parameters for that sample number. In automatic mode an equilibration delay between samples for gradient chromatography may be set by depressing "equilibration delay — total time remaining" and entering the desired parameters. Additionally, the number of injections of each sample may be varied from 1-9 utilizing "number of injections — inj remaining" entry key and entering the desired parameter. Thereafter pressing the "RUN" key will secure the desired operation automatically.

Assuming the carousel in place, the operation begins.

The carousel 470 may now be picked up, by opening RAD 9 to drop the carousel piston 472 and RAD 10 to pick up the carousel 470. The carousel is now driven to locate the fiducial or first position. It may then be driven by its stepper motor 462 to position the first sample bottle under the injection needle 250.

If desired, a purge may precede a run. The system may accomplish different types of purges. For example, to purge the sample loop 248 and needle 250, the computer causes RAD 8 to close, RAD 6 to open, and drive the needle down, say, into an empty bottle location. RAD 1 is closed, but RAD 2 is opened to cause drain valve 246 to close. Eluent now flows not only through primary line 234 and injection valve 240 to the column, but also through branch 244, sample loop 248 and needle 250.

To purge the branch 247 and assure liquid in syringe 264, RAD 6 is closed and RAD 8 is opened, RAD 7 remaining closed, thus placing needle opening 251 in sealed position in lower seal 372. RAD 1 is closed and RAD 2 is closed so that both normally open high pressure inlet liquid valve 240 and liquid syringe valve 246 are open. RAD 3 is opened to open normally closed liquid drain valve 266. Now eluent will flow through high pressure liquid valves 240 and 246 and low pressure liquid valve 266 to drain. Before this purge, the syringe may be driven to its closed position and afterwards retracted, and if desired, worked to assure that the syringe is liquid filled.

Also if desired, the branch from junction 265 to the check valve may be purged. With the valves conditioned as described in the last preceding paragraph except that RAD 3 is closed to leave normally closed valve 266 closed, the pressure from the pump 236 may be increased to overcome the 125 psig setting of the check valve 268. A purge of the line from the junction to the check valve 268 follows. Another purge is decribed below.

The run may now begin, under control of the computer 200. The position of the needle 250 and needle piston 344 in the up position may be verified by computer 200 pulse to an LED sensor (not shown) positioned for that purpose. RAD 1 and RAD 8 are closed to close valve 240 and to keep the needle in sealed position. RAD 1 is opened so that high pressure liquid valve 240 is closed. Turn RAD 8 on again to hold the needle in raised, sealed position. Open RAD 3 to open valve 266 and leave RAD 2 closed so that valve 246 remains open to vent system pressure in the sample loop 248 and in branch 247. Now RAD 3 is closed to close valve 266 again. Valve 246 remains open. Turn on the vacuum by opening RAD 5, and open RAD 4 for needle wash. Drive the needle 250 down by opening RAD 6 and closing RAD 8.

The needle 250 now pierces the septum of the selected sample bottle and rests with its opening 251 immersed in the sample. Next valve 254 is closed by turning off RAD 4, to prevent excess wash solution resulting in drip.

When purging the syringe may be left up (advanced) at a beginning point. Now the syringe 264 is retracted the requisite distance by stepping motor 262 to give the number of microliters of sample for injection called for in the microcomputer 200 memory for the particular bottle position. The advance or retraction per turn of the syringe is controlled by the thread ratio of the screw nut for the syringe drive and the volume of each unit movement readily calculated from the syringe diameter.

The computer can therefore control the syringe drive 262 to give the desired volume to be taken in. The desired number of microliters is now in the needle 250 and coil 249. Close RAD 4 to turn off the wash.

RAD 6 is turned off and RAD 8 is opened to drive the needle psiton to its stop and test position with needle opening 251 sealed. The initial analogue-to-digital reading from the bubble sensor 216 Bourdon tube 360 is now stored in a first computer register for comparison. The syringe drive is advanced by small steps to compress the liquid in the space enclosed between sealed opening 251 and the syringe. Essentially the volume of the enclosed space is slightly reduced. Change in volume resulting from straightening the Bourdon tube is a second order effect. A new pressure reading is now stored in a second register and compared to the storage in the first register. If the reading difference is equivalent to less than 30 psig, the process is continued, by again stepping drive 262, again storing the new reading in the second register and comparing it to the first. Meanwhile, there is stored in the computer the number of repetitions of this process, until the difference in readings equals, or exceeds, 30 psig. If this number of increments of drive is less than a predetermined number, $x$, the bubble indication is negative and the sample injection is continued. If the number is greater, a bubble check routine may be followed as described hereinafter.

Thus if the number is less than $x$, close the syringe valve 246 by opening RAD 2. Release the injection piston upward drive by closing RAD 8. Open RAD 7 to drive the cross-pin 430 to allow the needle piston 344 to go on up. Open RAD 8 to drive the needle piston 344 to its uppermost position. The needle opening 251 is now opposed to the annular space 325. RAD 1 is closed to open sample valve 240 and the injection of the sample begins.

If the number is greater than $x$, but less than some number $y$, also in computer memory, inclusion of a relatively small bubble is indicated. With the needle in the bubble check position i.e. with opening 251 sealed against lower seal 372, retract the syringe 264 to its initial position (initial digital reading) and again check for the bubble. If the indication is still present, syringe valve 246 being still open, the sample may be restored to the same sample vial by driving down piston 344 (open RAD 6), and advance the syringe to initial position. Again retract the syringe to enter sample of desired size and repeat the bubble test above. Note that the process of washing the needle 250 by operating RAD 4 and RAD 5 as heretofore described is repeated each time the needle 250 is driven down. If again indicated, while needle opening 251 is sealed (as at seal 372), because the bubble may be in the path between the syringe 264 and the check valve 268, a portion of this path may be cleared by closing RAD 1 to open the inlet valve 240. As the needle opening 251 remains sealed, liquid is driven out the check valve 268 to drain. Check valve pressure is set at 125 psig.

The entire procedure of driving the needle down to immerse the opening in the sample, ejecting sample into the same bottle, withdrawing the sample by the syringe, and testing again for bubble inclusion is repeated. If the test is negative, that is, no bubble inclusion is indicated, injection of the sample into the column may proceed as decribed above.

If the test is positive, a further purge including the sample loop 248 may now take place. RAD 8 is opened, the needle is raised to inject position with opening 251 facing the annular space 325. RAD 1 is open to close inlet valve 240. Syringe valve 246 is open (RAD 2 closed). If desired, for the purpose RAD 3 may also be opened at this time to open valve 266. Now, the resistance to flow in the path through sample loop 248 opens syringe valve 246 and drain valve 266 is less than the resistance to flow on the column side of the injection valve 242. Hence, eluent (solvent) washes out the paths from the pump through the back-flowing through the sample loop 248 to the drain. This procedure will flush any bubble in the sample. Again, a sample may be withdrawn from the same bottle or vial for another trial.

If in the foregoing tests, the number of steps required to achieve a pressure difference indication by Bourdon tube 360 from the initial pressure to 30 psig is greater than $y$, the indication is that there is a large bubble in the closed space. The needle is driven down, the syringe driven to its initial position to replace sample, if any, into the container, and retracted for one more trial. If the same result is reached, the indication is that the bottle or vial 522 is empty or contains insufficient sample. The needle is driven down and whatever contained in the sample loop ejected by driving the syringe to initial position, the needle withdrawn and washed, and the carousel advanced to the next bottle on the program. The system thus described is embodied in a system sold under the trademark WISP by the assignee of this application.

If the number $x$ is based on a difference of 30 psig, the number may be found in this fashion. Place in the line a suitable pressure gauge. Instead of the column use a suitable restrictor (small diameter line). Take a reading of the position of the Bourdon tube with suitable liquid or eluent with the pump working to produce some suitable pressure, say 30 psig. Increase the pressure by increasing the action of pump 236 with the liquid or eluent until the gauge shows 60 psig. Take a second reading of the Bourdon tube position. Now cause the piston 344 to be driven up (open RAD 6). Close RAD 7. Close high pressure inlet valve 240 (open RAD 1). High pressure sample valve 246 should be open (RAD 2 closed). Check the initial reading of the Bourdon tube to be the same as at the 30 psig, as initially above. Step the syringe drive 262 by stepping its stepping motor until the second Bourdon reading above at 60 psig is duplicated, counting the steps in computer memory or otherwise, and the resultant count gives the number $x$. Y may be similarly found by withdrawing air into the sample loop instead of liquid and following a similar process.

As described, the count of the number of incremental steps or changes in volume, closing the syringe to achieve the predetermined pressure, are used as a criterior or measure of bubble presence. The pressure could be sensed or measured directly and the change in pressure after a certain or predetermined change in volume could also be used to indicate presence or absence of bubble, a large pressure indicating no bubble. The former procedure is preferred because it is more easily implemented by computer programming, more readily adapted to the use of the Bourdon tube sensor which may be more accurately read to pressure differences, and the desired delimiting counts $x$ and $y$ have proved to be rather readily arrived at.

What is claimed is:

1. In a liquid chromatographic system, the combination comprising:
    a sample conduit,
    a pressure sensor coupled to said conduit,
    means for forming an enclosed space including said conduit,
    means for changing the volume of said enclosed space by increments starting from a first volume to change the pressure applied to said conduit with sample enclosed by increments starting from a first pressure,
    whereby the incremental changes in pressure sensed by said sensor resulting from said volume changes afford an indication of bubble inclusion in said sample.

2. The combination as claimed in claim 1, further comprising means to count the number of incremental changes in volume required first to reach a change in pressure equal to or greater than a predetermined pressure.

3. The combination as claimed in claim 2, further comprising means responsive to said count being greater than or equal to a predetermined count to eject said sample.

4. The combination claimed in claim 2, further comprising means responsive to said count the number of incremental changes being greater than or equal to a predetermined count to count a second time such increments of volume starting from said first volume.

5. The combination as claimed in claim 4, further comprising means to eject said sample in response to said count of increments a second time exceeding said predetermined count.

6. In a liquid chromatographic system, the combination comprising:
    a sample conduit,
    a pressure sensor coupled to said conduit,
    means for entering a liquid sample in said sample conduit,
    means for forming an enclosed space including said conduit,
    means for changing the volume of said enclosed space to change the pressure applied to said conduit with sample enclosed,
    whereby the change in pressure sensed by said sensor resulting from said volume change affords an indication of bubble inclusion in said enclosed space.

7. The combination as claimed in claim 6, said pressure sensor comprising a Bourdon tube.

8. The combination as claimed in claim 7, said pressure sensor comprising a Bourdon tube, a light source partially interrupted by said tube, in an amount dependent on the pressure sensor by the tube, and a light sensing element receiving the uninterrupted portion of the partially interrupted light.

9. The combination as claimed in claim 8, further comprising an analogue-to-digital converter coupled to said light sensing element to have a digital output responsive to the light sensed by the light sensing element.

10. In a liquid chromatographic system,
    a sample conduit,
    means communicating with said conduit to enter a sample of liquid therein comprising a needle having a bore, said bore having an opening,
    a syringe communicating with said conduit,
    a pressure sensor coupled to said conduit to sense the pressure in said conduit,
    means to seal said opening,
    means to actuate said syringe which the said opening is sealed with the said seal to change the volume enclosed between syringe, conduit, and opening, whereby the change in pressure sensed by said sensor resulting from said volume change affords an indication of bubble inclusion in said sample.

11. In a liquid chromatographic system, the combination comprising:
a sample conduit,
a pressure sensor coupled to said sample conduit,
a needle having a bore communicating with said conduit, said bore having an opening,
means to move said needle downward to a first position to immerse said opening in a liquid sample,
means to move said needle upward to a second position at which said opening is fully withdrawn from said sample,
means to stop said needle at an intermediate position between said opening immersed position and said opening withdrawn position, said sleeve providing a seal for said opening at said intermediate position,
means to actuate said syringe while said needle is positioned in said intermediate position and said opening sealed, thereby to change the volume enclosed between said seal, said bore, said conduit, and said syringe,
whereby the change in pressure sensed by said sensor resulting from said volume change affords an indication of bubble inclusion.

12. A combination as claimed in claim 11, said means to actuate said needle comprising a stepping motor.

13. A combination as claimed in claim 11, said means to stop said needle comprising a cross-pin having two dimensions, the larger of said dimensions affording a stop to stop said needle at said intermediate position.

14. A combination as claimed in claim 11, said means to move said needle to said positions comprising a piston carrying said needle.

15. A combination as claimed in claim 14, said combination comprising a stop for said piston, said stop having two positions in one of which the stop stops upward movement of said piston to stop said needle at the fully withdrawn position and the other of which stop positions stops said needle in said intermediate position.

16. In a liquid chromatographic system, the combination comprising:
a sample conduit,
a pressure sensor coupled to said sample conduit,
a needle having a bore communicating with said conduit, said bore having an opening,
means to position said needle downward at a first position to immerse said opening in a liquid sample,
means to position said needle at a second position at which said needle is withdrawn from said sample,
means to position said needle at a third position,
a sleeve within which said needle moves in its travel to said positions, said sleeve providing a seal at said needle third position,
means to actuate said syringe while said needle is positioned in said third position thereby to change the volume enclosed between said seal, said bore, said conduit and said syringe,
whereby change in pressure sensed by said sensor resulting from said volume change affords an indication of bubble inclusion.

17. A combination as claimed in claim 16, said third needle position being intermediate between said other two positions.

18. In a liquid chromatographic system wherein a primary conduit is arranged to carry liquid eluent from a pump to an injection valve and thence to a chromatographic volume and a sample conduit is arranged to be back-filled at an opening with a sample and placed in parallel with said primary conduit with the opening adjacent said injection valve, the improvement comprising:
means to close a space including the space within said conduit including means to seal said opening,
means to decrease the volume enclosed by said space, and
a pressure sensing means to sense the change in pressure resultant from said change in enclosed volume,
thereby to give an indication of bubble inclusion.

19. In a system having the improvement as claimed in claim 18, the said means to decrease the volume comprising a syringe.

20. In a system having the improvement as claimed in claim 18, said means to decrease volume comprising a means to change said volume by increments.

21. In a system having the improvement as claimed in claim 20, further comprising a computer means for storing a predetermined tally, means to count the number of increments required to first equal or exceed a predetermined pressure resultant from said changes, in volume, means to compare said count with said tally,
whereby a count less than said tally is a negative indication of bubble inclusion and a count greater than said tally indicates a positive indication of bubble inclusion.

22. In a liquid chromatograph system, a method of testing for bubble inclusion in a liquid sample comprising the steps of:
withdrawing a liquid sample from a sample source into a sample line,
then closing the sample line,
compressing the sample by a selected incremental volume to increase the pressure on the sample,
and sensing the resultant pressure change in the sample line,
thereby to derive an indication of bubble inclusion.

23. A method as claimed in claim 22, further comprising to repeating the step of incrementally compressing the sample,
the number of times required for the increased pressure to first equal or exceed a predetermined pressure to derive said indication.

24. A method as claimed in claim 22 further comprising repeating the step of incrementally compressing the sample, tallying each incremental increase, and comparing the number of tallies required for the increased pressure to first equal or exceed a predetermined pressure with a predetermined tally, to derive a positive or negative indication of bubble inclusion in accordance with whether said number of required tallies is (a) equal to or greater than said predetermined tally or (b) less than said predetermined tally.

25. In a liquid chromatograph system, a method of testing for bubble inclusion in a sample comprising the steps of:
placing the sample in a closed space,
changing the volume of said closed space while the sample remains closed therein,
and measuring the pressure change resulting from the change in volume to derive an indication of the presence or absence of bubble within the sample.

* * * * *